United States Patent [19]
Swierkowski

[11] Patent Number: 6,110,332
[45] Date of Patent: Aug. 29, 2000

[54] T-LOAD MICROCHANNEL ARRAY AND FABRICATION METHOD

[75] Inventor: Stefan P. Swierkowski, Livermore, Calif.

[73] Assignee: The Regents of the University of California, Oakland, Calif.

[21] Appl. No.: 09/178,778

[22] Filed: Oct. 26, 1998

[51] Int. Cl.[7] .................................................. C25B 9/00
[52] U.S. Cl. ..................... 204/242; 204/269; 205/665; 239/589
[58] Field of Search ........................ 239/1, 533.1, 549, 239/562, 553, 589, 590, 690; 310/328; 204/242, 269, 454–456; 205/665

[56] References Cited

U.S. PATENT DOCUMENTS

| | | | |
|---|---|---|---|
| 5,603,351 | 2/1997 | Cherukuri et al. | 204/269 |
| 5,746,901 | 5/1998 | Balch et al. | 204/456 |
| 5,858,188 | 1/1999 | Soane et al. | 204/454 |
| 5,871,158 | 2/1999 | Frazier | 239/589 |
| 5,877,580 | 3/1999 | Swierkowski | 310/328 |
| 5,900,130 | 5/1999 | Benvegnu et al. | 204/454 |
| 5,980,704 | 11/1999 | Cherukuri et al. | 204/269 |

*Primary Examiner*—Andres Kashnikow
*Assistant Examiner*—Dinh Q. Nguyen
*Attorney, Agent, or Firm*—L. E. Carnahan; Alan H. Thompson

[57] ABSTRACT

A three-dimensional (3-D) T-load for planar microchannel arrays for electrophoresis, for example, which enables sample injection directly onto a plane perpendicular to the microchannels' axis, at their ends. This is accomplished by forming input wells that extend beyond the ends of the microchannel thereby eliminating the right angle connection from the input well into the end of the microchannel. In addition, the T-load input well eases the placement of electrode in or adjacent the well and thus enables very efficient reproducible electrokinetic (ek) injection. The T-load input well eliminates the prior input well/microchannel alignment concerns, since the input well can be drilled after the top and bottom microchannel plates are bonded together. The T-load input well may extend partially or entirely through the bottom microchannel plate which enables more efficient gel and solution flushing, and also enables placement of multiple electrodes to assist in the ek sample injection.

28 Claims, 2 Drawing Sheets

T-LOAD MICROCHANNEL ARRAY AND FABRICATION METHOD

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to microchannel arrays, particularly to the input wells for microchannel arrays for electrophoresis and more particularly to a T-load input well geometry for microchannel arrays and method of fabrication.

Current emerging alternative methods to commercial slab-gel electrophoresis (e.g., for DNA sequencing) are systems based on discrete drift channels. One type is bundles of discrete glass micro-capillaries. Another type consists of one dimensional, integrated arrays of microchannels patterned in bonded glass plate pairs, such as described and claimed in U.S. application Ser. No. 08/772,639 filed Dec. 23, 1996, entitled Micromachined Chemical Jet Dispenser, and assigned to the same assignee. The input sample insertion geometry of the microchannel array prior type of analysis system (e.g., electrophoresis array), involves a right angle connection to the microchannel from the sample input well. This results in a three-dimensional (3-D) injection volume of the sample onto the end of the drift gel in the microchannel, which, in turn, is a fundamental limit of resolution; the gel-loading buffer fluid or sample interface is defined by convection and diffusion and is difficult to control because the input well or hole in the top plate overlaps the microchannel end in the bottom plate. The above-referenced integrated array type system requires fabricating a microchannel groove or bottom plate, and also a macro-hole capping plate; the capping plate completes the microchannel and also must be highly precision drilled for the input/output holes, and also precision aligned to the microchannel bottom plate for glass fusion bonding to assure alignment of the input wells with the ends of the microchannels.

It has been determined that the highest resolution can be obtained with electrokinetic (ek) loading directly onto a plane perpendicular to a micro-capillary axis at its end. Such high resolution could not be accomplished with the right angle connection of the microchannel end to the input well utilized in the prior system. The present invention provides a geometrical solution and method of use to enable loading directly onto a plane perpendicular to the end of the microchannels. Thus the present invention involves a new 3-D input well geometry comprising a T-load for planar, high density, integrated, microchannel arrays. The input well of the present invention also enables two-dimensional (e.g., titer plate format) sample input and efficient parallel operations and minimal input/output port space on the plates. The 3-D input well of the present invention extends past the ends of the micro-channel and partially or completely through the bottom or grooved microchannel plate; one input well embodiment being termed a "blind T-load" with the other input well embodiment being termed a "thru T-load."

SUMMARY OF THE INVENTION

It is an object of the present invention to provide an improved input well geometry for microchannel arrays.

A further object of the invention is to provide input wells for microchannel arrays which allow sample injection directly onto a plane perpendicular to the input axes of microchannel arrays, which avoids volumetric or plug types of T-load, implemented with intersecting microchannels.

Another object of the invention is to provide a 3-D T-load input well/microchannel interconnection, and simultaneously maintaining 2-D titer plates sample input format.

Another object of the invention is to provide a method for fabricating microchannel input wells which eliminate the prior right angle volumetric connection.

Another object of the invention is to provide a new geometry, a T-load arrangement, for planar microchannel arrays, such as utilized for electrophoresis.

Another object of the invention is to provide a 3-D T-load microchannel array and fabrication method that enables efficient two-dimensional input ports in the plane of the top plate that also allows sample injection directly onto a plane perpendicular to ends of the microchannels; i.e., perpendicular to the axes of the microchannels.

Another object of the invention is to provide a loading sequence and fabrication procedure that enables efficient parallel 2-D (e.g., titer plate format) sample insertion and electrokinetic injection by using manifold type input and input-waste reservoirs.

Another object of the invention is to provide a T-load geometry for sample input wells using either a blind T-load or thru T-load configuration.

Other objects and advantages of the present invention will become apparent from the following description and accompanying drawings. The invention involves a new geometry, a T-load, input well for planar microchannel arrays, and a method of fabrication. The T-load input wells enable efficient two-dimensional input ports that allow sample ek injection directly onto a plane perpendicular to the axes of the microchannels at their ends. The fabrication procedure and loading sequence of the present invention enables efficient parallel 2-D (e.g., titer plate format) sample insertion and electrokinetic injection by using manifold type input wells and input-waste reservoir. Efficient reproducible electrokinetic injection can be accomplished without the need for remote external probes by the use of multiple electrodes placed inside the manifold, and electrodes at the bonded interface or along the wall of the input wells. The T-load geometry input wells of the present invention may be of a blind T-load configuration or a thru T-load configuration, and the T-load input wells can be formed after the two microchannel plates, for example, are bonded together.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention is directed to a new geometry for input wells of microchannel arrays, such as used for electrophoresis, chemical flow injection analysis, and electrokinetic injection, etc. The new input well geometry is a 3-D T-load microchannel array and two embodiments are hereinafter described, one a blind T-load, and the other a thru T-load, each of which eliminate the right angle connection of the input well with an end of a microchannel, and provide for sample injection directly onto a microchannel on a plane perpendicular to the axis of the microchannels. The fabrication method and loading sequence of the T-load input wells enables efficient 2-D (e.g., titer plate format) sample insertion and electrokinetic injection by using manifold type input and input-waste reservoirs. The T-load geometry of the input wells has enabled high resolution with electrokinetic loading directly onto a plane perpendicular to that of the microchannels.

Figure 1:
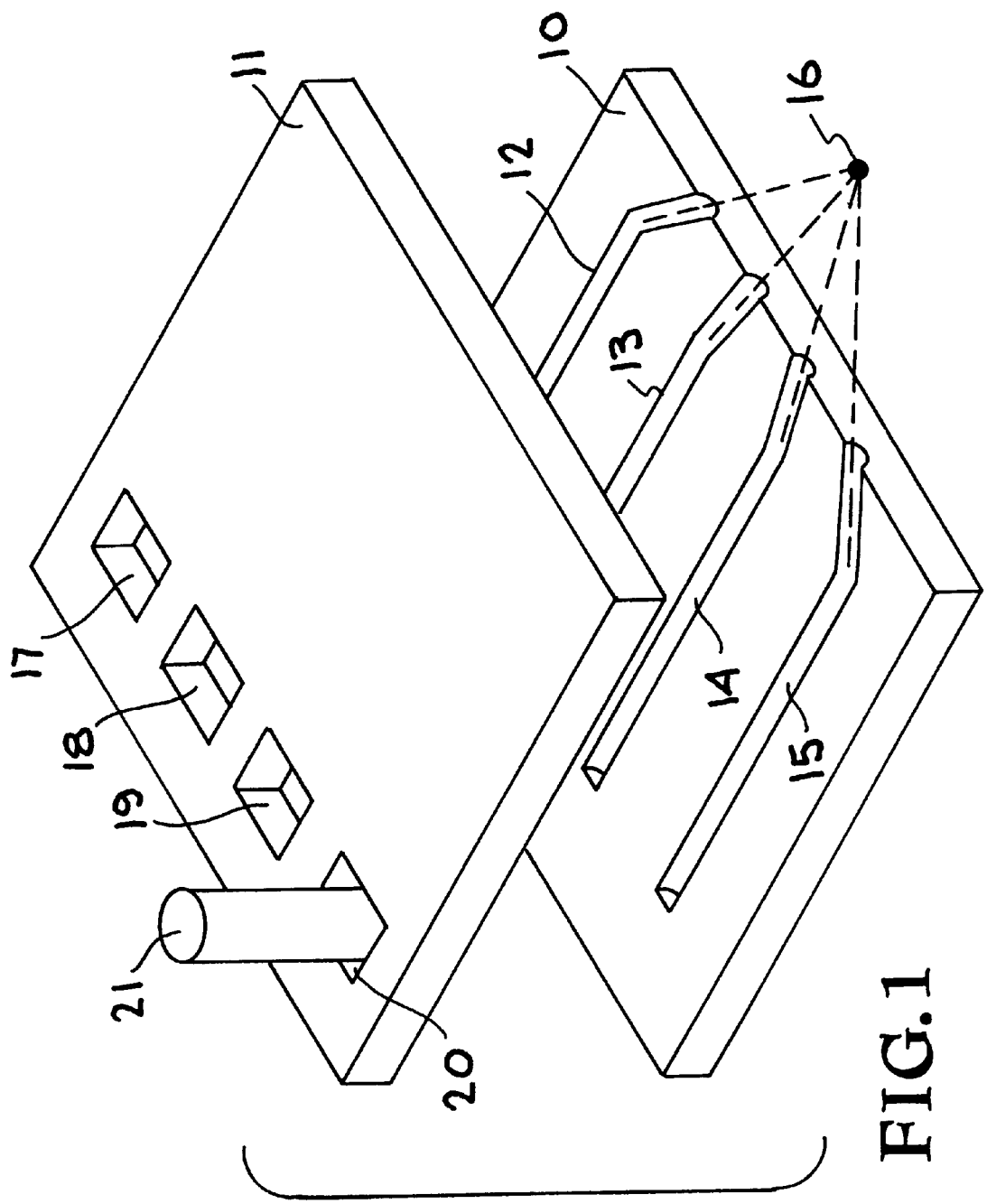
FIG. 1 is an exploded, schematic illustration of microchannel plate having an integrated array of microchannels formed in a bottom of the pair of plates.

FIG. 1 is an exploded view of a microchannel plate of a type similar to that of above-referenced application Ser. No. 08/772,639 where the lower or bottom plate or member contains an array of microchannels and the upper or top plate or member contains input wells for the microchannels and control means therefore. The top and bottom plates 10 and 11 may, for example, be composed of glass or plastic. The bottom plate or member 10 contains a plurality of microchannels 12, 13, 14, and 15 which, in this embodiment, are configured to discharge onto a focus point 16. The top plate or member 11 is provided with four square or circular input wells 17, 18, 19, and 20, an optional fill pipe 21 is shown inserted into input well 20. When plates 10 and 11 are bonded together, input wells 17–20 are aligned with input ends of microchannels 11–15.

Figure 2:
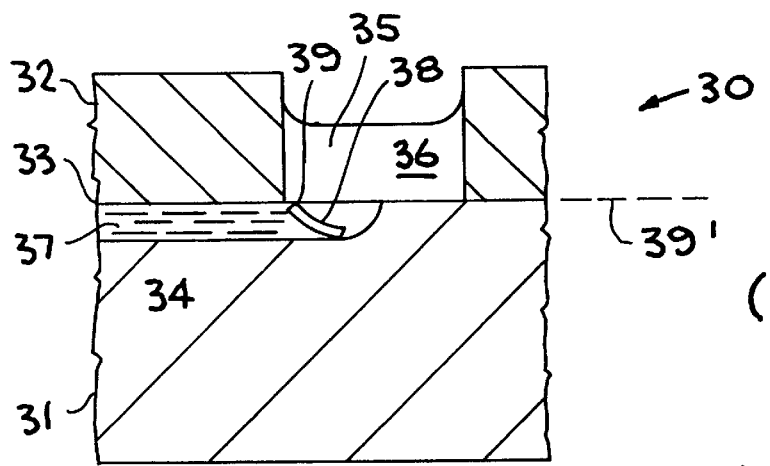
FIG. 2 is a cross-sectional view of a typical prior art input well for microchannel plates, such as that of FIG. 1.

The prior input well geometry for microchannel arrays is of an L-load configuration, as shown in FIG. 2, wherein a cross-section of a microchannel plate generally indicated at 30 is illustrated. The microchannel plate 30 consists of a lower or bottom plate or member 31 and an upper or top plate 32, which are bonded together as indicated at 33 and with bottom plate 31 having an array of microchannels 34 form therein, only one shown, and top plate 32 having a plurality of input wells 35, only one shown, containing a sample or buffer material 36. As known in the art, the microchannels 34 contain a gel 37, and thus there is a gel-buffer interface, as indicated at 38, adjacent the end 39 of microchannel 34. As seen in FIG. 2, the input well 35 overlaps the microchannel 34 and terminates adjacent the upper surface of microchannel, whereby the connection fluid passage from the input well 35 defines a plane perpendicular to the plane of interconnections of plates 31 and 32 and to the plane the microchannel 34, as indicated by the dotted line 39', and to the microchannel 34 involves a right angle; this results in a three-dimensional injection volume of the sample or buffer material onto the end of the drift gel in the microchannel 34, which in turn is a fundamental limit of resolution; the gel-loading buffer fluid interface 38 is defined by convection and diffusion and is difficult to control because the input well overlaps the microchannel end 39.

In fabrication of the L-load well of FIG. 2, the microchannels 34 are formed, as by etching, in the upper surface of bottom plate 31, which may be composed of glass or plastic, the input wells 35 are formed in the upper plate 32, as by drilling or etching, the upper plate 32 being composed of glass or plastic, whereafter the plates 31 and 32 are fusion bonded or otherwise secured together following precise alignment of the input wells with the ends of the microchannels. Thus fabrication of the microchannel plate 30 of FIG. 2 is alignment critical, which increases the cost of manufacture.

The present invention substantially eases the difficulty and cost of prior fabrication by different drilling procedures and alignment requirements, described in greater detail hereinafter. The present invention involves new 3-D geometry input wells, the T-load (either "blind' or "thru") for planar, high density, integrated, microchannel arrays. The result of the T-load input well geometry is that the microchannels end abruptly in a plane perpendicular to the microchannel; the right angle channel connection is eliminated. In the prior (FIG. 2) L-load arrangement, the ends of the microchannels overlap the input well; gel flush and loading buffer solution use smears out the gel-buffer fluid interface as determined by both convection and diffusion. The use of the T-loads of this invention (FIGS. 3 and 4) allows the excess gel to more easily be sheared off and rinsed out and establish a fluid interface at the end of the microchannel, albeit still limited by diffusion. The blind T-load (FIG. 3) can be formed by a second shallow machining or etching operation in the bottom plate, which merely extends the length of the input well beyond the end of the microchannel. Alternately, the FIG. 3 blind T-load input wells can be fabricated by drilling the bonded plate pair simply over the ends of the microchannels, which eases the accuracy of the drilling since it only needs to shear off the ends of the microchannels; the drilling itself is much easier and less costly than the precise alignment procedures required for the prior L-load input well.

Figure 3:
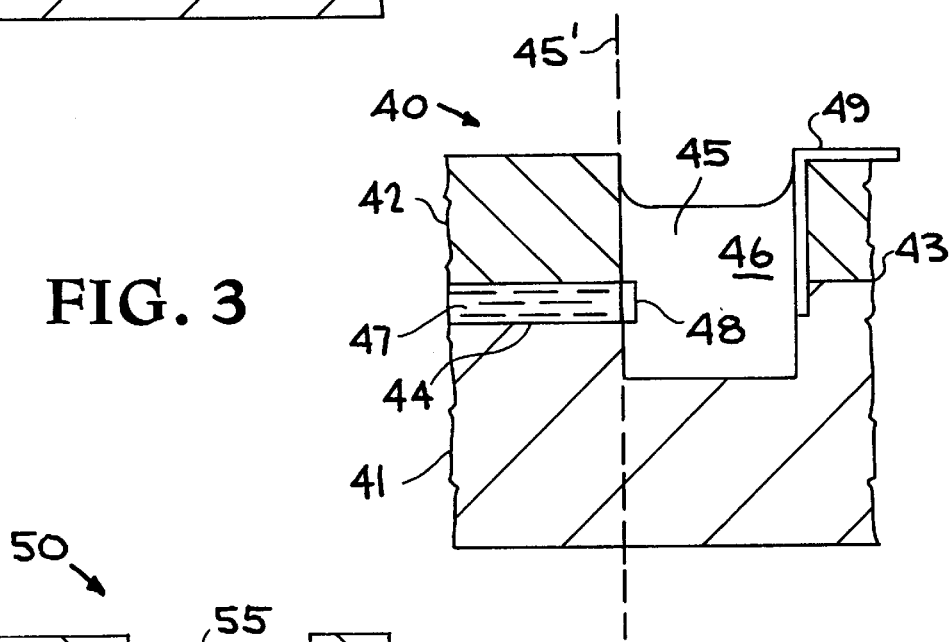
FIG. 3 is a cross-sectional view of an embodiment of a blind T-load input well made in accordance with the present invention.

Referring now to FIG. 3, an embodiment of the "blind" T-load input well is illustrated in cross-section. The term "blind" is from the input well only extending partially into the bottom plate. As shown, a microchannel plate 40 comprises bottom and top plates 41 and 42, bonded together at 43, with bottom plate 41 having microchannels 44, only one shown, and an input well 45 is formed in the top plate 42 and a portion of bottom plate 41 containing a buffer or sample fluid 46. In this "blind" T-load input well arrangement, a gel-buffer interface 48 between a gel 47 in the microchannel 44 and the buffer or sample fluid 46 in input well 45 is located along a side wall surface of the input well 45, the end of microchannel 44 being sheared off so as to be perpendicular to the axis of the input well 45, which enables sample or buffer material injection onto a plane perpendicular to-and at the end of-the drift or microchannel 44. As seen in FIG. 3, the input microchannel 44 defines a plane perpendicular to the plane of the input well 45, indicated at 45'. One or more electrodes 49 may be formed or deposited on a wall surface of input well 45 and opposite the end of microchannel 44 to assist in electrokinetic sample injection.

Figure 4:
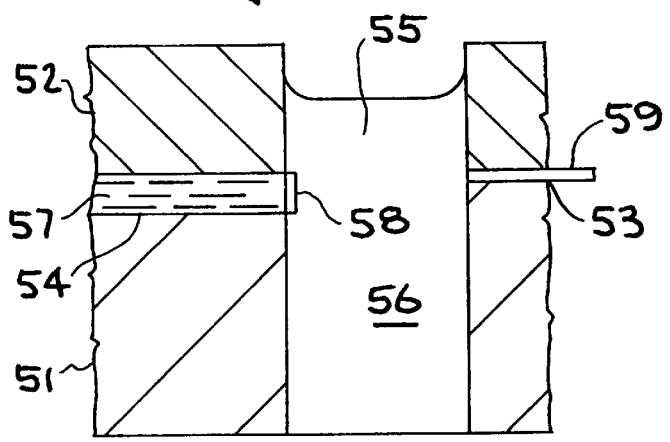
FIG. 4 is a cross-sectional view of an embodiment of a thru T-load input well made in accordance with the present invention.

Referring now to FIG. 4, which illustrates in cross-section an embodiment of a "thru" T-load input well, wherein the well extends through both the top and bottom plates. As shown, the microchannel plate 50 comprises a bottom plate 51 and a top plate 52 bonded together at 53. As in FIG. 3, the bottom plate includes an array or microchannels 54, only one shown, and an array of input wells 55, only one shown, is formed in top and bottom plates 52 and 51 and which contains a buffer or sample fluid or material 56, and the microchannel 54 contains a gel 57, with a gel-buffer interface 58 being located on the side wall surface of the input well 55, as described above with respect to FIG. 3. An electrode 59 is formed or deposited adjacent the interface or bond 53 and opposite the end of microchannel 54. The primary difference between the "thru" T-load of FIG. 4 and the "blind" T-load of FIG. 3, is that the input well extends "thru" both the top plate 52 and the bottom plate 51, and the electrode 59 is located intermediate the plates 51 and 52. As in the FIG. 3 embodiment, the drilling accuracy is eased since the drilling to form the input wells can be carried out after the top and bottom plates are bonded, thus eliminating the alignment concerns associated with the fabrication of the prior L-load input well. However, the "thru" T-load input well of FIG. 4 can also be formed prior to bonding of the top and bottom plates by forming, such as by drilling or etching holes in each plate, which can be aligned prior to bonding.

Key features of the 3-D T-load input wells of the present invention include:

1. The blind T-load (FIG. 3) can be used in current instruments, since it only accesses the top side; the same pipette flushing will much more effectively shear off and clear out the excess gel from gel filling operation.

2. The thru T-load (FIG. 4) has several attractive features: (a) the bottom can utilize a waste liquid collection manifold that can be left in place; (b) the top flush can be done with a top manifold of rinse solution with a single, simple outer seal around the input array, thus eliminating placing of flushing tips accurately; the common flushing action should make the rinsing procedure more reproducible and uniform; (c) multiple electrodes can be placed inside the bottom external manifold (not shown) to assist in the electrokinetic sample injection, and also to serve as isolation getters to present samples from migrating from one well to another, via the manifold, and (d) an additional electrode at the bond interface, or along the input wall, opposing the channel end, enables very efficient reproducible electrokinetic injection without the need of probes, especially if the sample is injected from a titer plate-injector head, such as described and claimed in copending U.S. apllication Ser. No. 09/178,779, filed Oct. 26, 1998, entitled "An Integrated titer Plate-Injector Head for Microdrop Array Storage and Transfer," assigned to the same assignee. It is thus seen that the present invention provides a significant advance in the field of microchannel arrays. The invention may be utilized, for example, in chemical electrophoresis, chemical flow injection analysis, liquid chromatography, enhanced electrokinetic injection, and chemical reaction microcapillary flow systems.

While particular embodiments, potential applications, materials, parameters, etc., have been described and/or illustrated, such is not intended to be limiting. Modifications and changes may become apparent to those skilled in the art, and it is intended that the invention be limited only by the scope of the appended claims.

The invention claimed is:

1. In a microchannel plate having at least one microchannel and at least one input well, the improvement comprising:

said at least one input well having a side wall surface which extends beyond said at least one microchannel enabling sample injection from said at least one input well onto a plane perpendicular to the at least one microchannel and at an end of the at least one input well.

2. The improvement of claim 1, wherein an interface between a gel in the at least one microchannel and a material in said at least one input well is located on said side wall surface of said at least one input wall.

3. The improvement of claim 1, wherein said at least one input well extends only partially through said microchannel plate to form a blind input well.

4. The improvement of claim 3, additionally including at least one electrode extending into said at least one input well along a side wall surface opposite the end of said at least one microchannel.

5. The improvement of claim 1, wherein said at least one input well extends entirely through said microchannel plate to form a thru input well.

6. The improvement of claim 5, additionally including at least one electrode extending into said at least one input well on a side wall surface opposite the end of said at least one microchannel.

7. The improvement of claim 1, additionally including at least one electrode located on a wall surface of said at least one input well and opposite said end of said at least one microchannel.

8. The microchannel plate of claim 1, including an array of microchannels and an array of input wells, each microchannel having an end located along a side wall surface of an associated input well and substantially perpendicular to said microchannel.

9. The microchannel plate of claim 8, wherein said array of input wells is selected from the group consisting of blind input wells and thru input wells.

10. The microchannel plate of claim 8, additionally including at least one electrode located in at least one of said array of input wells and located on a side wall surface opposite said end of at least one of said microchannels.

11. A microchannel plate comprising a top plate and a bottom plate secured together, said bottom plate having at least one microchannel formed therein, said top and bottom plates having at least one input well therein having a side wall perpendicular to an end of said at least one microchannel.

12. A microchannel plate of claim 11, additionally including at least one electrode in said at least one input well and located on a side wall opposite said at least one microchannel.

13. The microchannel plate of claim 11, wherein said at least one input well is selected from a group consisting of blind T-load wells and thru T-load wells.

14. The microchannel plate of claim 13, wherein said at least one input well is a blind T-load well which extends through said top plate and partially through said bottom plate.

15. The microchannel plate of claim 14, additionally including at least one electrode located on a side wall surface of said blind T-load input well and opposite said end of said at least one microchannel.

16. The microchannel plate of claim 15, wherein said at least one electrode extends from on top of said top plate along a side wall surface of said at least one input well.

17. The microchannel plate of claim 13, wherein said at least one input well is a thru T-load input well which extends through both of said top and bottom plates.

18. The microchannel plate of claim 17, additionally including at least one electrode located on a side wall surface of said thru T-load input well and opposite said end of said at least one microchannel.

19. The microchannel plate of claim 18, wherein said at least one electrode extends between said top and bottom plates into said input well.

20. The microchannel plate of claim 13, having an array of microchannels and an array of input wells, each input well having a side wall substantially perpendicular to an end of an associated microchannel.

21. The microchannel plate of claim 20, wherein each of said array of input wells is composed of an input well selected from the group of blind T-load and thru T-load input wells.

22. The microchannel plate of claim 20, wherein at least one of said array of input wells additionally including at least one electrode located on an opposite side wall surface from said end of an associated microchannel.

23. In a method for fabricating a microchannel plate having a top and bottom plate with an array of microchannels formed in the bottom plate, the improvement comprising:

forming an input well at an end of each microchannel which extends through the top plate and at least partially through the bottom plate, whereby the ends of each of the microchannels are located in and substantially perpendicular to side wall surfaces of the associated input well.

24. The improvement of claim 23, wherein the input wells extend through both the top and bottom plates.

25. The improvement of claim 23, wherein in forming of the input wells is carried out following bonding together of the top and bottom plates.

26. The improvement of claim 23, additionally including forming at least one electrode on a side wall surface of at least one of the input wells opposite the end of the associated microchannel.

27. The improvement of claim 26, wherein the forming of the at least one electrode is carried out along a top surface of the top plate and extending into the input well to at least a location opposite the end of the microchannel.

28. The improvement of claim 26, wherein the forming of the at least one electrode is carried out prior to bonding of the top and bottom plates and is formed along an adjacent surface of at least one of the top and bottom plates so as to be intermediate the plates and extends into the input well on a side wall opposite the end of the microchannel.

* * * * *